US006998392B2

(12) United States Patent
Clandinin et al.

(10) Patent No.: US 6,998,392 B2
(45) Date of Patent: Feb. 14, 2006

(54) FORMULATION TO TREAT OR PREVENT PARASITIC INFECTION

(75) Inventors: Michael Thomas Clandinin, Edmonton (CA); Miyoung Suh, Edmonton (CA); Miodrag Belosevic, Edmonton (CA)

(73) Assignee: MTI Meta Tech Inc., Edmonton (CA)

( * ) Notice: Subject to any disclaimer, the term of this patent is extended or adjusted under 35 U.S.C. 154(b) by 387 days.

(21) Appl. No.: 10/404,095

(22) Filed: Apr. 2, 2003

(65) Prior Publication Data

US 2004/0198694 A1 Oct. 7, 2004

(51) Int. Cl.
  A61K 37/715 (2006.01)
  A61K 31/70 (2006.01)
  A61K 31/7012 (2006.01)
  A61K 31/7028 (2006.01)

(52) U.S. Cl. ............................ 514/54; 514/25; 514/23; 536/4.1; 536/55.1; 536/18.7; 536/123.1

(58) Field of Classification Search ................... 514/54, 514/25, 23; 54/23; 536/4.1, 55.1, 18.7, 536/123.1
See application file for complete search history.

(56) References Cited

U.S. PATENT DOCUMENTS 4,762,822 A * 8/1988 Ettinger ........................ 514/25

OTHER PUBLICATIONS

Isasi et al. (Acta Tropica (1999), 73(3), 295-302) (Absract Sent).*
Sigma Chemical Company Catalog (Biochemicals Organic Compounds for Research and Diagnostic Reagents), 1993 edition (Abstract Sent).*
Belosevic and Faubert, "*Giardi muris*: Correclation between Oral Dosage, Course of Infection, and Trophozoite Distribution in the Mouse Small Intestine", 1983, Exp. Parasitol., 56:93-100.
Bouhours and Bouhours, "Developmental Changes of Hematoside of Rat Small Intestine", 1983, J. Biol. Chem., 258:299-304.
Brown and Rose, "Sorting of GPI-Anchored Proteins to Glycolipid-Enriched Membrane Subdomains during Transport to the Apical Cell Surface", 1992, Cell, 68:533-544.
Buret et al., "Growth, activites of enzymes in the small intestine, and ultrastructure of microvillous border in gerbils infected with *Giardia duodenalis*", 1991, Parasitol Res., 77:109-114.
Clandinin and Yamashiro, "Dietary Factors Affecting the Incidence of Dietary Fat-Induced Myocardial Lesions", 1982, J. Nutr., 112: 825-828.

Daniels And Belosevic, "Disaccharidase activity in male and female C57BL/6 mice infected with *Giardia muris*", 1995, Parasitol Res., 81 : 143-147.
Diamond et al., "A new medium for the axenic cultivation of *Entamoeba histolytica* and other *Entamoeba*", 1978, Trans. R. Soc. Trop. Med. Hyg., 72:431-432.
Farthing, "Giardiasis", 1996, Gastro. Clin. North Am., 25: 493-515.
Folch And Sloane-Stanley, "A Simple Method for the Isolation and Purification of Total Lipides from Animal Tissues", 1957, J. Biol. Chem., 226:497-509.
Forstner and Wherrett, "Plasma Membrane and Mucosal Glycosphingolipids in the Rat Intestine", 1973, Biochim. Biophys. Acta., 306:446-459.
Gibson et al., "*Giardia lamblia*: Incorporation of Free and Conjugated Fatty Acids into Glycerol-Based Phospholipids", 1999, Exp. Parasitol., 92:1-11.
Gillin, "*Giardia lambia*: The Role of Conjugated and Unconjugated Bile Salts in Killing by Human Milk". 1987, Exp. Parasitol., 63:74-83.
Gillin et al., "Cholate-Dependent Killing of *Giardia lamblia* by Human Milk", 1985, Infect. Immun., 47:619-622.
Gillon et al., "Features of small intestinal pathology (epithelial cell kinetics, intraepithelial lymphocytes, disaccharidases) in a primary Giardia muris infection", 1982, Gut., 23:498-506.
Holmgren et al., "Comparison of Receptors for Cholera and *Escherichia coli* Enterotoxins in Human Intestine", 1985, Gasteroenterology, 89:27-35.
Iwamori et al., "Gangliosides of Various Rat Tissues: Distribution of Ganglio-$N$-Tetraose-Containing Gangliosides and Tissue-Characteristic Composition of Gangliosides", 1984, J. Biochem., 95:761-770.
Jarroll et al., "Lipid and Carbohydrate Metabolism of *Giardia lamblia*", 1981, Mol. Biochem. Parasitol., 2:187-196.
Jennnings et al., "The Significance of Lowered Jejunal Disaccharidase Levels", 1976, Aust. NZ J. Med. 6:556-560.
Karlsson, "Microbial recognition of target-cell glycoconjugates", 1995, Curr. Opin. Structur. Bio., 5:622-635.

(Continued)

Primary Examiner—Elvis O. Price
Assistant Examiner—Michael C. Henry
(74) Attorney, Agent, or Firm—Kathleen E. Marsman; Borden Ladner Gervals LLP

(57) ABSTRACT

The invention provides a formulation for treatment or prevention of a parasitic infection such as a protozoan or helminths infection, for example: *Giardia*. The formulation comprises at least one ganglioside, which may be selected from the group consisting of: GD3, GM1, GM2, GM3, GD1b, NANA, and sialic acid. The formulation may be used to supplement foods or liquids, for example: infant formula, baby food, baby cereal, juice, dehydrated camping food, or bottled water.

10 Claims, 14 Drawing Sheets

OTHER PUBLICATIONS

Kyogashima et al., "*Escherichia coli* K99 Binds to *N*-Glycolylsialoparagloboside and *N*-Glycolyl-GM3 Found in Piglet Small Intestine", 1989, Arch. Biochem. Biophys., 270: 391-397.

Laegreid and Otnaess, "Trace Amounts of Ganglioside GM1 in Human Milk Inhibit Enterotoxins from *Vibrio Cholerae* and *Escherichia Coli*", 1987, Life Sci., 40:55-62.

Ortega-Barria et al., "Growth Inhibition of the Intestinal Parasite *Giardia lamblia* by a Dietary Lectin Is Associated with Arrest of the Cell Cycle", 1994, J. Exp. Med., 94:2283-2288.

Reiner et al., "Human Milk Kills *Giardia lamblia* by Generating Toxic Lipolytic Products", 1986, J. Infect. Dis., 154:825-832.

Roberts-Thomson et al., "Giardiasis in the Mouse: an Animal Model", 1976, Gastroenterology, 71:57-61.

Rohrer et al., "Killing of *Giardia lamblia* by Human Milk Is Mediated by Unsaturated Fatty Acids", 1986, Antimicrob. Agents Chemother., 30:254-257.

Rolsma et al., "Structure and Function of a Ganglioside Receptor for Porcine Rotavirus", 1998, J. Virol., 72:9079-9091.

Rueda et al., "Changes during Lactation in Ganglioside Distribution in Human Milk from Mothers Delivering Preterm and Term Infants", 1996, Biol. Chem., 377:599-601.

Rueda et al., "Addition of gangliosides to an adapted milk formula modifies levels of fecal *Escherichia coli* in preterm newborn infants", 1998, J. Pediatr., 133:90-94

Sorice et al., "Evidence for the existence of ganglioside molecules in the antigen of *Entamoeba histolytica*", 1996, Parasite Immunol., 18:133-137.

Stevens et al., "Uptake and Cellular Localization of Exogenous Lipids by *Giardia lamblia*, a Primitive Eukaryote", 1997, Exp. Parasitol., 86:133-143.

Underdown et al., "Giardiasis in Mice: Studies on the Characteristics of Chronic Infection in C3H/He MICE", 1981, J. Immunol., 126:669-672.

Vazquez et al., "Dietary gangliosides positively modulate the percentages of Th1 and Th2 lymphocyte subsets in small intestine of mice at weaning", 2001, BioFactors, 15:1-9.

Walterspiel et al., "Secretory Anti-*Giardia lamblia* Antibodies in Human Milk: Protective Effect Against Diarrhea", 1994, Pediatrics, 93:28-31.

Watarai et al., "Gangliosides as a Possible Receptor on the Bovine Erythrocytes for *Theileria sergenti*", 1995, J. Vet. Med. Sci., 57:17-22.

Williams et al., "The Use of Sep-Pak™ $C_{18}$ Cartridges During the Isolation of Gangliosides", 1980, J. Neurochem., 35:266-269.

Wolfe, 1992, Clin. Microbiol. Rev., 5:93-100.

\* cited by examiner

FORMULATION TO TREAT OR PREVENT PARASITIC INFECTION

FIELD OF THE INVENTION

The present invention relates generally to a formulation for treatment or prevention of parasitic infection, such as protozoan or helminth infection.

BACKGROUND OF THE INVENTION

In North America, the incidence of Protozoan infection is 2–3% overall, 30–50% in children's day care situations. Outside of North America, incidence of Protozoan infection has been reported as high as 40–60% in developing countries. Some waterborne outbreaks occur without the availability of effective drugs for treatment.

Protozoan infection is usually treated with drugs, which are costly and may have dangerous side effects in certain individuals. Individuals with immunodeficiency diseases, such as HIV and some cancers, have a high susceptibility to protozoan infection and these individuals cannot tolerate the toxic side effects of drugs currently used to treat protozoan infection.

Transmission of a pathogenic microorganism from an animals to a human, termed zoonosis, is responsible for significant outbreaks of infectious disease in human populations. An outbreak of *Cryptosporidium* in Milwaukee (Wis.), during which more than 400,000 people became infected, was believed to be caused by contamination of the water reservoir by cattle feces containing viable *Cryptosporidium parvum* oocytes. A similar outbreak occurred in North Battleford (Canada) in 2002. The water borne transmission of *E. coli*, an intestinal bacterium, caused significant morbidity and mortality of humans in Walkerton (Canada). Outbreaks of "beaver fever" caused by the protozoan parasite, *Giardia lamblia*, have occurred in Banff and Edmonton (Canada) in the recent past. Host nutritional and immune status is closely related with the disease course of giardiasis.

*Giardia* is a protozoan parasite that inhabits the upper small intestine of a wide range of vertebrates including humans. It is spread via contaminated food and water and by direct host to host contact. After entering the host, the parasites emerge from the cysts, and adhere to the epithelial brush border of the small intestine as flagellated trophozoites. The trophozoites multiply in the small intestine, eventually encysts and are passed in the feces as infectious cysts. The number of cysts released in feces was reported to be related to the trophozoite burden in the small intestine and degree of pathology observed during the infection (Belosevic and Faubert, 1983). A full citation for each prior art document referenced herein is provided below.

Clinical manifestations of giardiasis range from asymptomatic to symptomatic. Symptoms include diarrhea, weight loss, abdominal distension, vomiting and abdominal pain (Farthing 1996; Wolfe 1992). The severity of symptoms may vary and was found to be related to the initial number of cysts ingested, the age of the host, and the state of the host immune system. Disaccharidase deficiency causing malabsorption has been observed in both humans (Jennnings 1976) and animals (Buret et al., 1991; Daniels and Belosevic, 1995; Gillon et al., 1982), and was related to the parasite burden in the small intestine (Daniels and Belosevic, 1995).

Gangliosides, sialic acid-containing glycosphingolipids, are located at the surface of the cell membrane with the hydrophilic oligosaccharide chain extending into the extracellular space. Glycosphingolipid constitutes approximately 20% of the brush border membrane lipids (Forstner and Wherrett, 1973). The dominant ganglioside is GM3 (Daniels and Belosevic, 1995) which is 7 times more concentrated in the neonatal compared to adult intestine of rats (Bouhours and Bouhours, 1983). The specific physiological roles of gangliosides are poorly understood, however, studies showed that gangliosides provide binding sites for a wide range of pathogens including viruses, bacteria and fungi (Holmgren et al., 1985; Kyogashima et al., 1989; Laegreid and Otnaess, 1987; and Rolsma et al., 1998). For example, ganglioside GM3 acts as a natural receptor in pig small intestine for rotavirus (Rolsma et al., 1998) and the enterotoxigenic bacteria *Escherichia coli* (*E. coli*) K99 (Kyogashima et al., 1989). Ganglioside GM1 in human intestine (Holmgren et al., 1985) and in human milk (Laegreid and Otnaess, 1987) also provides receptors for enterotoxin of *Vibrio cholerae* and the heat-labile *E. coli*, thereby acting as a physiological barrier for protection against these enteric infections.

Preterm newborn infants fed ganglioside supplemented formula at a concentration of 1.43 mg/100 Kcal, were shown to have significantly lower numbers of *E. coli* and bifidobacteria in the feces (Rueda et al., 1998). Previous studies showed that gangliosides exist in clusters in the plasma membrane forming glycosphingolipid enriched domains (Buret et al., 1991), and that these domains are the preferential interaction sites between target cells and pathogens (Karlsson, 1995).

Decreased prevalence of giardiasis among infants fed breast milk containing high titers of anti-Giardia secretory IgA (sIgA) has been reported (Walterspiel et al., 1994). Studies showed that non-immune components of human milk such as conjugated bile salts (Gillin, 1987), unsaturated fatty acids (Rohrer et al., 1986) and free fatty acids (Reiner et al., 1986) may be involved in the elimination of the parasites. Although breast milk also contains a significant amount of gangliosides (Rueda et al., 1996), it has never been examined whether gangliosides may play a protective role in giardiasis.

It is desirable to find a compound, a class of compounds, or composition active against giardiasis.

Prior art references referred to herein are provided below:
Belosevic and Faubert. 1983. Exp. Parasitol. 56:93–100.
Bouhours and Bouhours. 1983. J. Biol. Chem. 258:299–304.
Brown and Rose. 1992. Cell. 68:533–544.
Buret et al., 1991. Parasitol Res. 77:109–114.
Clandinin and Yamashiro. 1982. J. Nutr. 112: 825–828.
Daniels and Belosevic. 1995. Parasitol Res. 81:143–147.
Diamond et al., 1978. Trans. R. Soc. Trop. Med. Hyg. 72:431–432.
Farthing. 1996. Giardiasis. Gastro. Clin. North Am. 25:493–515.
Folch and Sloane-Stanley. 1957. J. Biol. Chem. 226: 497–509.
Forstner and Wherrett. 1973. Biochim. Biophys. Acta. 306:446–459.
Gibson et al., 1999. Exp. Parasitol. 92:1–11.
Gillin. 1987. Exp. Parasitol. 63:74–83
Gillin et al., 1985. Infect. Immun. 47:619–622.
Gillon et al., 1982. Gut. 23:498–506.
Holmgren et al., 1985. Gasteroenterology. 89:27–35.
Iwamori et al., 1984. J. Biochem. 95:761–770.
Jarrol et al., 1981. Mol. Biochem. Parasitol. 2:187–196.
Jennnings et al., 1976. Aust. NZ J. Med. 6:556–560.
Karlsson 1995. Curr. Opin. Structur. Bio.5:622–635.

Kyogashima et al., 1989. Arch. Biochem. Biophys. 270: 391–397.
Laegreid and Otnaess. 1987. Life Sci. 40:55–62.
Ortega-Barria et al., 1994. J. Exp. Med. 94:2283–2288.
Reiner et al., 1986. J. Infect. Dis. 154:825–832.
Roberts-Thomson et al., 1976. Gastroenterology. 71:57–61.
Rohrer et al., 1986. Antimicrob. Agents Chemother. 30:254–257.
Rolsma et al., 1998. J. Virol. 72:9079–9091.
Rueda et al., 1996. Biol. Chem. 377:599–601.
Rueda et al., 1998. J. Pediatr. 133:90–94.
Sorice et al., 1996. Parasite Immunol. 18:133–137.
Stevens et al., 1997. Exp. Parasitol. 86:133–143.
Suzuki, K. 1964. Life Sci. 3:1227–1233.
Underdown et al., 1981. J. Immunol.; 126:669–672.
Vazquez et al., 2001. BioFactors. 15:1–9.
Walterspiel et al., 1994. Pediatrics. 93:28–31.
Watarai et al., 1995. J. Vet. Med. Sci. 57:17–22.
Williams et al., 1980. J. Neurochem. 35:266–269.
Wolfe 1992. Clin. Microbiol. Rev. 5:93–100.

Abbreviations used herein are as follows: GM1: $II^3$ NeuAc-GgOse$_4$Cer; GM2: $II^3$ NeuAc-GgOse$_3$Cer; GM3: $II^3$ NeuAc-LacCer; GD1b: II3 (NeuAc)$_2$-GgOse$_4$Cer; GD3: $II^{(NeuAc)}{}_2$-LacCer; E. Coli: Escherichia coli; Gang-High: High concentration of ganglioside; Gang-Low: Low concentration of ganglioside; G: Giardia; LCPUFA: Long chain polyunsaturated fatty acids; NANA: N-Acetyl neuraminic acid; PBS: Phosphate buffered saline solution; SEM: Standard error of the mean; sIgA: Secretory immunoglobulin A; TG: Triglyceride; and TG+PUFA: Triglyceride containing polyunsaturated fatty acids.

SUMMARY OF THE INVENTION

It is an object of the present invention to provide a formulation, a compound, a class of compounds or a composition active in the treatment or prevention of a parasitic infection such as a protozoan or helminths infection, and particularly Giardia infection.

According to the invention, there is provided a formulation comprising at least one ganglioside for prevention or treatment of parasitic infection, such as a protozoan or helminths infection. The ganglioside maybe GD3, GM1, GM2, GM3, GD1b, NANA, sialic acid or other gangliosides, as are known in the art. A method of treating a parasitic infection, such as a protozoan or worm infection by providing a ganglioside to a subject in need thereof, and a use of a ganglioside in treating or preventing such an infection are also provided.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

Embodiments of the present invention will now be described, by way of example only, with reference to the attached Figures, wherein.

DETAILED DESCRIPTION

Figure 1:
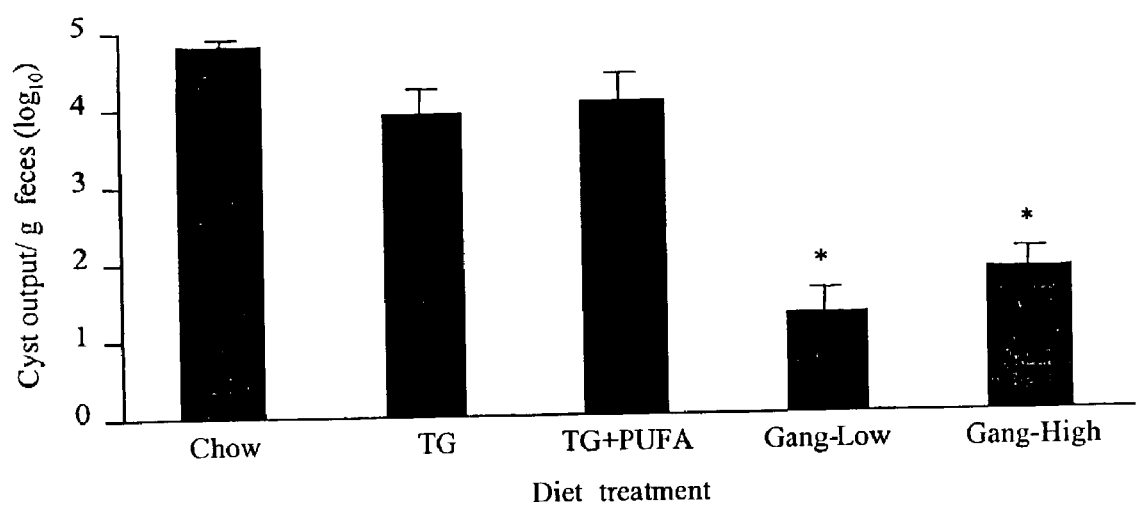
FIG. 1 illustrates the effect of dietary gangliosides on the average cyst output for 2 hour during the 25 days of *Giardia muris* infection in mice.

Generally, the present invention provides a formulation for treatment and prevention of a parasitic infection selected from either a protozoan or helminths infection, and which is particularly useful in preventing or treating Giardia infection. Protozoan parasites of the intestine include intestinal lobosea, intestinal sporozoea, and intestinal zoomastigophorea, to which *Giardia intestinalis* belongs. Other protozoa against which the invention is effective include, but are not limited to *Entamoeba histolytica, Cryptosporidium parvum, Eineria tenella*, other species of Eimeria, and *Balantidium coli*.

Infection by amoeboid parasites may be prevented or treated according to the invention. Helminth (worms) may include such intestinal parasites as intestinal nematoda, intestinal cestoidea or intestinal trematoda. Further, the parasites susceptible to the inventive formulation need not be limited to intestinal parasites.

The invention is based in the discovery of a ganglioside-containing composition, such as a milk-derived dietary component, that enhances the elimination of parasites in animals such as mice. The invention is also particularly useful in treating or preventing parasitic infection in human populations. Domestic animals and livestock also benefit from the inventive treatment against parasitic infection.

Experiments were done to assess the effects of this diet component isolated from milk on the course of *G. muris* infected mice in vivo and on the survival of *G. lamblia* in culture. These procedures were used to screen and identify bioactive components responsible for the prophylactic and therapeutic effect.

According to the invention, a ganglioside fraction, for example a fraction derived from milk, and referred to herein as "Fraction A" herein may be used.

The dosage amount of the ganglioside formulation according to the invention that may be used to treat or prevent parasitic infection can easily be determined by one of skill in the art. A daily or one-time only minimum dosage may be from microgram to milligram quantities. A higher level may have a greater effect where the exposure and likelihood of infection is increased. A formulation in food or fluid form having from 1 to 1000 ppm could easily be delivered to a subject in need thereof. A large range is possible, and no upper limit is required because the formulation does not display toxicity, and is not know to be toxic.

Fraction A is prepared by crude processes, and is available from a dairy food company in New Zealand. Fraction A is of variable lipid composition, and a specific exemplary composition is provided below with respect to Example 2. The inventors have further purified this crude fraction to isolate a bioactive complex lipid referred to as PROTOREX™ formulation. PROTOREX™, may vary in composition but is approximately 80% GD3; 9% GD1b, and 5% GM3 by weight, the remaining 6% being comprised of other gangliosides.

Other molecular forms of this complex lipid may be derived, according to the invention, with similar or even greater bioactive characteristics. According to one possible composition of the formulation used in the instant invention, PROTOREX™ contains one or more gangliosides, such as for example GD3, GM1, GM2, GM3, GD1b, NANA, and sialic acid and is bioactive against Giardia producing very high kill rates. In vitro killing is illustrated using very small quantities in culture.

Advantageously, the invention identifies components active in prevention and/or treatment of protozoan activity and allows for commercial isolation of a lipid fraction (or formulation) containing specific bioactive components. The anti-protozoan activity of this lipid fraction has not previously been described or illustrated. In particular, the formulation is effective against Giardia in vivo and in vitro, and provides an alternative to drug-based treatments currently used to treat protozoan infections. The formulation of the invention has little to no potential for toxicity or side effects.

Certain components of the formulation of the invention can be isolated from components of the present food supply, and thus would not need "drug" approval to be added to or to enriched new foods.

Gangliosides are known to be receptors for enterotoxic bacteria in the small intestine however, a role in gastrointestinal parasitic infections is not known. The invention illustrates that ganglioside supplementation is fatal to tropozoites of Giardia and thus can be used to treat or prevent Giardia infection. For example *Giardia muris* infection and growth of *Giardia lamblia* trophozoites can be mitigated. According to the invention, feeding ganglioside pre- and post infection is protective and therapeutic against Giardia infection. Replication of this parasite and/or cyst formation in the small intestine can be reduced, and gangliosides have a direct toxic effect on this parasite.

Ganglioside supplementation, or supplementation of a lipid fraction containing ganglioside can be used to treat or prevent protozoan infection, and is particularly effective against Giardia infection. The ganglioside or lipid fraction may be supplemented as a fortifier into existing foods, such as in infant formulas, baby foods, baby cereals, and follow-on formulas which may be used for children up to about 18 months of age. Further, supplementation may also be useful in juices or other fluids packaged particularly for toddlers or older children (for example, which may be useful at daycare centers), or in cereals as a coating or powdered sprinkle. Such foods may advantageously be those which are appealing to children, as this could be used to prevent protozoan infection in a daycare or school setting.

Bottled water or other bottled drinks may be supplemented with the inventive formulation, for use by children or adults of a group susceptible to protozoan infection.

In addition to being supplemented into food, the formulation may be provided in a liquid, gel, powder, tablet, pill or capsule form. Tablet, pill or capsule form may appeal to older children and adults, and would avoid the need to consume a food or beverage. The supplement may also be added to pet foods, or supplements, or to foods directed to other domesticated animals. In some instances, it may also be desirable to supplement the formulation to livestock.

Alternatively, foods for travellers or campers (such as dehydrated foods or beverages) may be supplemented with the formulation according to the invention, to avoid infection while camping or travelling in areas having questionable or unknown cleanliness in the water supply. The formulation may be provided as a powder or liquid form in a plastic or otherwise scalable pouch.

In underprivileged areas of the world (third world countries), infant formula supplementation, and supplementation for children may be used to ward off infection and sustain health.

Rural or less affluent areas where untreated or well-derived water is used may benefit from supplementation of the inventive formulation in food, or in a tablet or fluid form. Seasonal drinks for spring and summer may benefit from supplementation with the inventive formulation, as this is often when parasitic activity is heightened due to increased livestock and animal activity.

Without wishing to be limited by theory, the efficacy of the invention against parasites, including protozoa and worms, appears to be based in part on a metabolic inhibition of the parasite. The mode of action of gangliosides may also be a combination of a direct lytic effect on the parasite and metabolic inhibition. The invention as described and discussed herein illustrates that both mechanisms may act in concert because of the observation that the parasites are lysed, but also because those parasites that survive are not dividing, or not dividing as rapidly.

EXAMPLE 1

Ganglioside Supplementation Alters Giardia Infection of Mice in vivo, and Growth of Trophozoites in vitro.

Gangliosides are known to be receptors for enterotoxic bacteria in the small intestine. However, a role in gastrointestinal parasitic infections has not previously been established, prior to this invention. This Example examines whether a ganglioside supplemented diet affects the course of *Giardia muris* infection in mice and growth of *Giardia lamblia* trophozoites in vitro.

Female CD-1 mice were fed one of five experimental diets: (i) standard lab chow as a control (Chow); (ii) semi-synthetic diets containing 20% (w/w) triglyceride based on the fat composition of a conventional infant formula (TG);

(iii) TG diet containing 20:4n-6 and 22:6n-3 (1.0% and 0.5%, w/w of fatty acids, TG+PUFA); (iv) TG diet containing ganglioside (0.1% w/w, Gang-Low); and (v) TG diet containing ganglioside (1.0% w/w of diet, Gang-High). After 2 weeks of feeding, mice were inoculated with *G. muris* by gastric intubation and fed the experimental diets during the course of the infection. Fresh feces were collected for 2 hours every 5 days for 25 days post infection for determination of cysts released in the feces. Trophozoites present in the small intestine were enumerated on day 10 post infection.

This Example reveals that, compared to mice fed the control diet, mice fed either Gang-High or Gang-Low diet exhibited significantly reduced cyst output in the feces during the course of the infection. The average cyst output during the course of the infection (25 days) in mice given ganglioside containing diet was significantly lower (3-$\log_{10}$ reduction) compared to control animals fed Chow diet. No differences were found in cyst output of mice fed the TG, TG+PUFA or Chow. The numbers of trophozoites in the small intestine of infected mice were also drastically reduced in mice fed Gang-High and Gang-Low diet in comparison to mice fed Chow diet. The results of in vitro growth studies using *G. lamblia* trophozoites indicate that gangliosides may be directly toxic to the parasites. The numbers of live trophozoites were significantly reduced after 24 and 48 hours of incubation in the presence of at least 14 µg/ml and 8 µg/ml ganglioside, respectively. These results indicate that feeding ganglioside pre- and post infection had a protective effect against Giardia infection by controlling parasite replication and/or cyst formation in the small intestine, and that gangliosides are directly toxic to the parasites. Details of this Example are provided below.

Introduction. In this Example, the effect of dietary ganglioside on the course of *G. muris* infection in mice was determined by enumerating cyst output in the feces and trophozoite burden in the small intestine of mice fed ganglioside supplemented diet. The effect of different ganglioside concentrations (ganglioside enriched preparation and isolated ganglioside fractions) on in vitro growth of *G. lamblia* (or *G. duodenalis*) trophozoites was also examined.

Materials and Methods. Methodology is provided below for the two main aspects of this Example, specifically: examining the effect of ganglioside supplemented diet on the course of *Giardia muris* infection; and examining the effect of a ganglioside enriched preparation and ganglioside fractions on growth of *Giardia lamblia* trophozoites in vitro.

Methods for Evaluating the Effect of Ganglioside Supplemented Diet on the Course of *Giardia muris* Infection. This study was approved by the University of Alberta Animal Ethics Committee. Five to six week old female pathogen free CD-1 mice weighing 20.4±1.1 g, were obtained from Charles River Laboratories (St. Constant, Quebec) and were randomly divided into 5 groups of 5 mice each. The control group was fed a standard lab chow diet (Chow), as shown in Table 1.

TABLE 1

| | Experimental Diets | | | | |
|---|---|---|---|---|---|
| | Chow[a] | TG[b] | TG + PUFA[c] | Gang-Low[d] | Gang-High |
| | | | (g/100 g) | | |
| Basal diet[e] | Chow | 80.0 | 80.0 | 80.0 | 80.0 |
| Fat | 5.0 | 20.0 | 20.0 | 20.0 | 20.0 |
| Triglyceride | 5.0 | 20.0 | 20.0 | 19.6 | 16.5 |

TABLE 1-continued

| | Experimental Diets | | | | |
|---|---|---|---|---|---|
| | Chow[a] | TG[b] | TG + PUFA[c] | Gang-Low[d] | Gang-High |
| | | | (g/100 g) | | |
| Gangliosides | — | — | — | 0.1 | 1.0 |
| Phospholipids | — | — | — | 0.25 | 2.5 |

[a]Standard mouse chow serving as a control.
[b]Fatty acid composition reflecting the fat blend of an existing infant formula.
[c]TG fat blend with addition of arachidonic acid (C20: 4n − 6) and docsahexaenoic acid (C22: 6n − 3) mixture.
[d]TG fat blend with ganglioside containing nutrients.
[e]Clandinin and Yamashiro (1982). TG, triglyceride; TG + PUFA, triglyceride containing long chain polyunsaturated fatty acids; Gang-Low, low concentration of ganglioside; Gang-High, high concentration of ganglioside.

The other 4 groups were fed semi-synthetic experimental diets (Clandinin and Yamashiro, 1982) containing 20% (w/w) fat as triglyceride. The fat composition of the semi-synthetic diet reflects the fat composition of a conventional infant formula providing a ratio of 18:2n-2 to 18:3n-3 of 7:1 (TG). Three additional experimental diets were prepared by addition of long chain polyunsaturated fatty acids, C20:4n-6 (1%, w/w) and C22:6n-3 (0.5%, w/w of total fatty acid) (TG+PUFA), or low (0.1% ganglioside, w/w of total diet, Gang-Low) or high (1% ganglioside, w/w of total diet, Gang-High) ganglioside preparation (New Zealand Dairy, New Zealand) to TG diet. The lipid composition of ganglioside preparation consists of about 45–50% (w/w) phospholipids and 15–20% (w/w) gangliosides. The ganglioside fraction contained GD3, GD1b, GM3 and other gangliosides (80%, 9%, 5% and 6% w/w, respectively). The ganglioside preparation also contained lactose and minerals (60–70%, 10–12% w/w, respectively) and the level of these amounts was adjusted in the basal diet as shown in Table 1.

After feeding for 2 weeks, animals were inoculated orally with 10,000 cysts of *G. muris* suspended in 0.2 ml of de-ionized water and were maintained on different diets during the course of the infection (25 days).

The following procedure was used to enumerate *G. muris* cysts in feces. Fresh feces from each mouse were collected for two hours between 7:00 am and 9:00 am every 5 days until day 25 post infection for determination of cysts released in the feces. Cysts were isolated using the sucrose gradient centrifugation as described by Roberts-Thompson et al. (1976), and enumerated using procedures described previously by Daniels and Belosevic (1995). Briefly, feces were weighed, emulsified in de-ionized water and gently layered on 1M sucrose solution in a glass test tube. Samples were centrifuged for 15 min at 400×g. The cysts present at the water-sucrose interface were carefully removed with a pipette and washed in de-ionized water by centrifugation for 10 min at 600×g. The supernatant was discarded and the pellet containing the cysts re-suspended in 1 ml of de-ionized water. Cysts were enumerated using a hemocytometer and expressed as number of cysts per gram of feces.

The following procedure was used to enumerate *G. muris* trophozoites in the small intestine. The enumeration of trophozoites present in the small intestine of 10 to 12 mice for each experimental group was done on day 10 post infection using the procedures we described previously by Daniels and Belosevic (1995). Briefly, the small intestine was removed and divided into 4 equal sections. Intestinal segments were placed in ice cold phosphate buffered saline (PBS, pH 7.2) and incubated on ice for 30 min. The intestinal segments were then slit longitudinally and mucosa scraped using glass microscope slides. The mucosal scrapings including the remainder of the intestinal segment were placed in 6 ml of ice cold PBS, mixed vigorously and filtered through double layer of moist cheese cloth. The volume of the filtered solution was adjusted to 6 ml and the total number of trophozoites in each segment determined using a hemocytometer.

Methods for Evaluating the Effect of Ganglioside Enriched Preparation and Ganglioside Fractions on Growth of *Giardia lamblia* Trophozoites in vitro. The following method was used for preparation of culture medium containing ganglioside. A preparation containing gangliosides was vortexed and sonicated (Sonic 300 Dismembrator™, Artek System Corp.) in 10 ml of TYI-S-33 culture medium, and further diluted by adding 990 ml of culture medium. This stock culture medium containing a known concentration of gangliosides was filtered in succession through Whatman™ No. 1 filter paper, 0.8 μm, 0.45 μm (Milli-Fil-P.F.™ Millipore Corp.), and 0.22 μm (Sterivex-GS™ filters with filling bell, Millipore Corp) filters connected to a peristaltic pump. This stock solution was kept at $-30°$ C. and was diluted on the day of inoculation.

*G. lamblia* (WB strain) trophozoites were cultured in Diamond's TYI-S-33 (Diamond et al., 1978.). *G. lamblia* trophozoites ($5 \times 10^5$) were inoculated in 12.5 cm$^2$ tissue culture flasks in the total volume of 40 ml. Nutrient stock solution containing gangliosides was diluted to provide a concentration of ganglioside (as N-Acetyl neuraminic acid amounts, NANA) at 0 (control), 0.001, 0.01, 1, 2, and 4 μg/ml. The cultures were incubated for 24 and 48 hr at 37° C. in 5% $CO_2$, and the number of live and dead (no flagellar movement) trophozoites determined using a hemocytometer.

Ganglioside (NANA) content was measured as described by Suzuki (1964). Gangliosides were then diluted using the culture medium and filtered as described above.

*G. lamblia* trophozoites ($5 \times 10^5$) were incubated for 24 hr and 48 hr with ganglioside fraction at the concentration of 0 (control), 4, 8, 10, 12, 14, 16 and 20 μg/ml in 12.5 cm$^2$ tissue culture flasks as described above.

Statistical analysis was conducted as follows. The effects of diets on *G. muris* infection by enumerating cyst output were examined in two independent experiments. Since no significant differences were found between the two experiments, the data from the two experiments were combined. Enumeration of *G. muris* trophozoites in the intestine of mice was determined. For both experiments enumerating cyst output and trophozoites, the effects of diets were analysed by one-way analysis of variance for each collection day. The effect of the ganglioside enriched preparation and ganglioside fractions on the replication of *G. lamblia* in vitro were carried out in duplicate and repeated 5 times and 3 times, respectively. The effect of ganglioside treatment was analysed by one way analysis of variance and Duncan's Multiple Range Test. All data were expressed as mean±standard error of the mean (SEM). Probability level of $P<0.01$ was considered significant.

Results. Each group of mice were fed one of the five experimental diets for 14 days before exposure to *G. muris* and during the course of the infection (25 days). The body weight of mice fed TG, TG+PUFA or Gang-Low diet increased slightly during the post infection experimental period, whereas those given standard lab chow (Chow) and Gang-High diet maintained their weight during the course of the infection, as shown in Table 2. Statistically significant increase in body weight was observed in mice fed TG+PUFA compared to those fed Chow or Gang-High diet.

TABLE 2

Effect of Experimental Diet on Body Weight*

| | Body weight (g) | | | | |
|---|---|---|---|---|---|
| | Chow | TG | TG + PUFA | Gang-Low | Gang-High |
| Days post infection** | | | | | |
| Day 0 | 25.2 ± 0.4 | 25.6 ± 0.3 | 26.2 ± 0.8 | 24.9 ± 0.7 | 24.9 ± 0.7 |
| Day 5 | 24.3 ± 0.3$^b$ | 26.4 ± 0.5$^{ab}$ | 26.8 ± 0.9$^a$ | 25.2 ± 0.6$^{ab}$ | 24.5 ± 0.9$^b$ |
| Day 10 | 24.5 ± 0.3$^b$ | 26.7 ± 0.7$^{ab}$ | 27.7 ± 1.0$^a$ | 25.8 ± 0.6$^{ab}$ | 24.8 ± 0.9$^b$ |
| Day 15 | 24.9 ± 0.2 | 26.9 ± 0.8 | 27.8 ± 1.0 | 26.0 ± 0.6 | 25.3 ± 0.9 |
| Day 20 | 25.0 ± 0.3$^c$ | 27.7 ± 1.0$^{ab}$ | 28.5 ± 1.1$^a$ | 26.6 ± 0.6$^{abc}$ | 25.6 ± 0.9$^{bc}$ |
| Day 25 | 24.8 ± 0.3$^b$ | 26.2 ± 1.2$^b$ | 31.1 ± 2.2$^a$ | 26.8 ± 1.0$^b$ | 25.0 ± 1.0$^b$ |

*The values (means ± SEM, n = 8 to 10 except day 25, n = 5) were from two independent experiments. Significant effects were identified by one-way analysis of variance procedures for diet on each day: day 5, p < 0.05; day 10, p < 0.03; day 20, p < 0.03; day 25, p < 0.02.
**Values within a row having a different letter indicate significant differences between experimental groups.

The following method was used for preparation of culture medium containing ganglioside fraction. Total lipids were extracted from the ganglioside enriched preparation using the Folch method (Folch et al., 1957). The ganglioside containing upper phase was transferred and the lower phase was washed once with Folch upper phase solution (chloroform/methanol/water, 3/48/47 by vol.). The combined ganglioside containing fractions were passed through Sep-Pak™ C18 reverse-phase cartridges (Waters Corporation, Milford, Mass., USA), eluted with methanol and chloroform and methanol 2:1 (v/v), and dried completely under vacuum at 23° C. using a rotary evaporator (Williams et al., 1980).

A ganglioside supplemented diet effected the course of *G. muris* infection. Two independent experiments were conducted to assess the effect of dietary ganglioside on the *G. muris* infection by measuring cyst output in CD-1 mice. Feeding mice diets containing different level of dietary gangliosides significantly affected *G. muris* infection.

In FIG. 1, the effect of dietary gangliosides on the average cyst output for 2 hours during the 25 days of *Giardia muris* infection in mice is illustrated. Values (means±SEM, n=8 to 10 except day 25, n=5) were from two independent experiments and represented average cysts produced in the feces from day 5 to 25 post infection. Significant effects of diets were identified by one-way analysis of variance procedures, p<0.00⁴. Values with * were significantly different from Chow, TG and TG+PUFA diets.

FIG. 1 shows that the average combined cyst output (logio) during the 25 days in mice fed either Gang-Low or Gang-High diet was 1.3±0.3 and 1.8±0.3 cysts/g feces, respectively, and that of mice fed Chow was 4.8±0.4 cysts/g feces. Animals fed TG or TG+PUFA diet released similar number of cysts in the feces compared to the control mice fed Chow diet.

Figure 2:
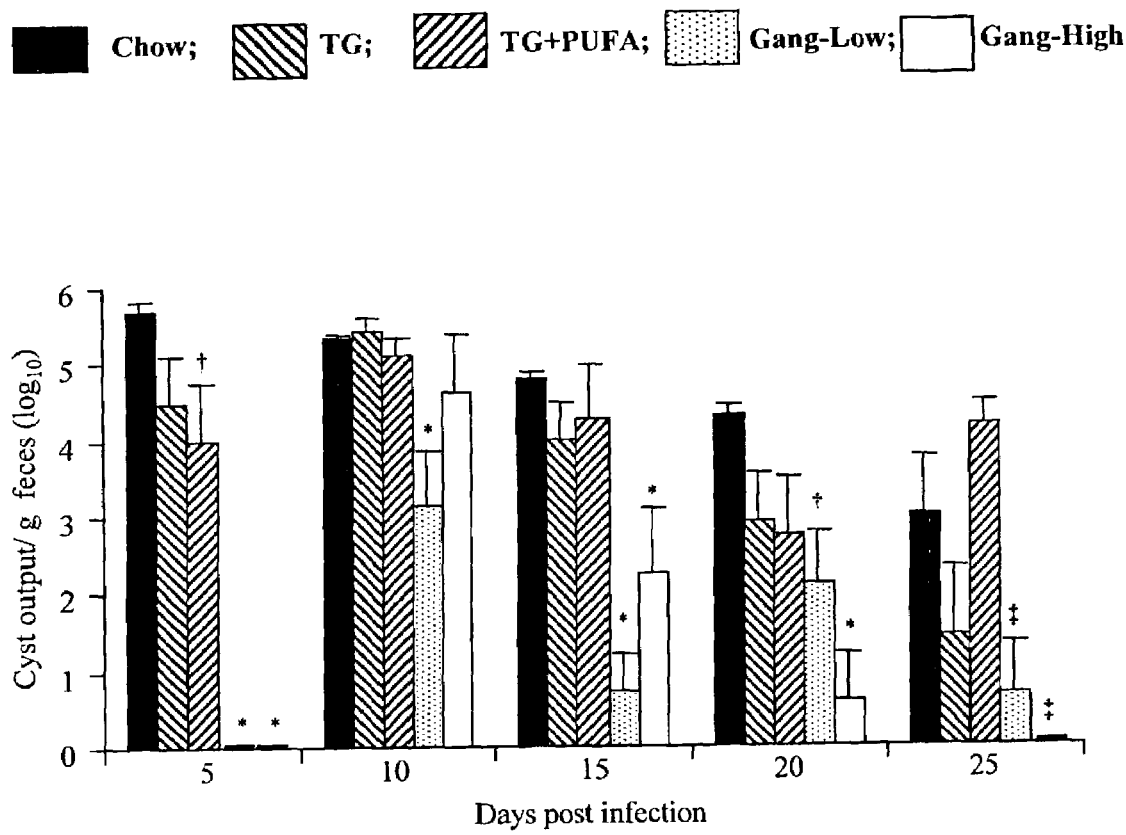
FIG. 2 depicts the effect of dietary gangliosides on the course of *Giardia nuris* infection in mice measured by cyst output in feces for up to 25 day s post infection.

In FIG. 2, the effect of dietary gangliosides on the course of *Giardia muris* infection in mice is measured by cyst output in feces. Values (means±SEM, n=8 to 10 except day 25, n=5) were from two independent experiments. Significant effects of diets were identified by one-way analysis of variance procedures on each post infection day: day 5, $p<0.0001$; day 10, $p<0.004$; day 15, $p<0.0001$; day 20, $p<0.003$; day 25, $p<0.004$. Values with * were significantly different from Chow, TG and TG+PUFA diets. Values with † were significantly different from Chow diet. Values with ‡ were significantly different from chow and TG+PUFA diets. Values given as (—) on day 5 and 25 post infection represents zero output.

FIG. 2 shows that the onset of cyst release in mice fed Gang-High and Gang-Low diets was delayed as indicated by lack of cyst release in these mice on day 5 post infection compared to other treatment groups. Mice fed either Gang-High or Gang-Low diet exhibited significantly reduced cyst output ($p<0.0001$) during the course of the infection. In all experimental groups, the highest cyst output was observed on day 10 post infection. No difference in the average cyst output were observed between mice fed Chow and mice fed TG or TG+PUFA diets, suggesting that triglyceride with and without long chain fatty acids did not influence the course of *G. muris* infection in mice. The duration of cyst release was also affected by Gang-High and Gang-Low diets. Eighty percent of mice fed Gang-High and 90% of mice fed Gang-Low diet did not release cysts in the feces on day 20 and 25 post infection, respectively, whereas the feces of most of mice in other experimental groups contained cysts.

Figure 3:
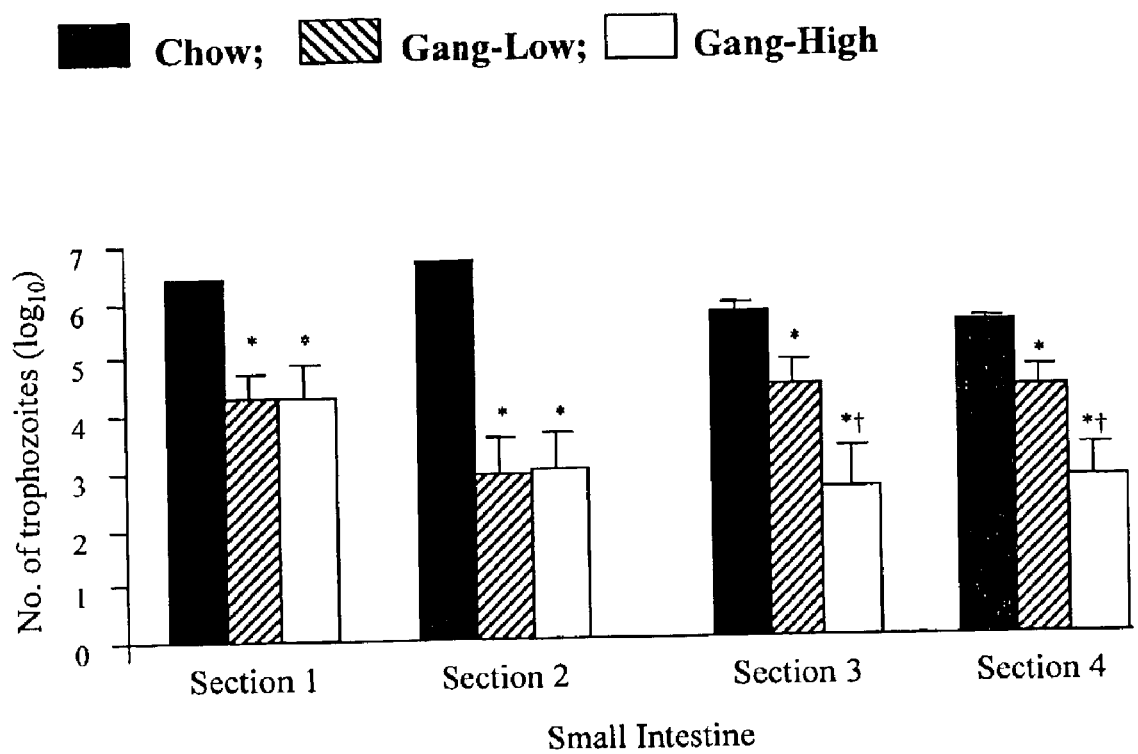
FIG. 3 illustrates the effect of dietary gangliosides on *Giardia muris* replication in four sections of the small intestine of mice at 10 days post infection.

FIG. 3 provides data showing the effect of dietary gangliosides on *Giardia muris* replication in the small intestine of mice at 10 days post infection. Values represent means±SEM of n=10 to 12. The enumeration of trophozoites present in the small was done on day 10 post infection. The small intestine was removed and divided into 4 equal sections. Significant effects of diet were identified in each section of small intestine by one-way analysis of variance procedures; Section 1, $p<0.001$; Section 2, $p<0.0001$; Section 3, $p<0.0002$; Section 4, $p<0.0002$. Values with * at each section were significantly different from chow. Values with † at each section were significantly different Gang-Low diet. Values where SEM is not shown indicates very small SEM.

FIG. 3 illustrates the effects of dietary gangliosides on the *G. muris* infection was determined by enumerating trophozoite load in the small intestine on day 10 post infection. Since no differences in cyst output were observed in animals fed TG or TG+PUFA diet compared to mice fed the Chow diet, only the ganglioside containing diets were tested in this experiment. Diet containing gangliosides significantly reduced the trophozoite load in the small intestine. The total numbers of trophozoites in all sections of small intestine were drastically reduced in mice fed either Gang-High or Gang-Low diet compared to mice fed the Chow diet. A further decrease in the number of trophozoites was observed in section 3 and 4 of the small intestine in mice fed Gang-High diet compared to mice fed Gang-Low diet. Taken together, these results indicate that dietary gangliosides significantly altered the course of *G. muris* infection in mice as indicated by: (i) delay in the onset of cyst release; (ii) reduced cyst output during the course of the infection; (iii) decrease in trophozoite load in the small intestine during the acute phase of infection; and (iv) accelerated elimination of the parasites from the host.

According to this Example, it is clear that a ganglioside enriched preparation and isolated ganglioside fractions have an effect on growth of *G. lamblia* trophozoites in vitro. To determine whether ganglioside containing nutrients inhibited parasite growth, this Example employed in vitro cultured WB strain of *G. lamblia*, which was initially isolated from a human host. Gangliosides (as NANA) were provided at the level of 0 (control), 0.001, 0.01, 1, 2, and 4 $\mu$g/ml to each flask containing $5\times10^5$ trophozoites and incubated for 24 hrs and 48 hours, as shown in Table 3.

TABLE 3

Effect of Ganglioside Enriched Preparation on the Growth of *Giardia lamblia* Trophozoites during 24 hr and 48 hr Incubation in vitro

|  | Live trophozoites[a] | | Dead trophozoites[b] | |
| --- | --- | --- | --- | --- |
| Significance | 24 hrs ($p < 0.01$) | 48 hrs ($p < 0.0001$) | 24 hrs ($p < 0.001$) | 48 hrs ($p < 0.0001$) |
| Ganglioside Conc. ($\mu$g/ml) | | | | |
| 0 | 100 | 100 | 1.6 ± 0.2 | 2.7 ± 0.6 |
| 0.001 | 101.8 ± 1.9 | 89.2 ± 7.2 | 2.7 ± 0.2 | 3.3 ± 0.4 |
| 0.01 | 102.2 ± 3.8 | 92.4 ± 5.2 | 1.5 ± 0.2 | 2.9 ± 0.6 |
| 0.1 | 101.1 ± 6.0 | 96.1 ± 2.1 | 2.7 ± 0.5 | 4.2 ± 0.7 |
| 1 | 106.5 ± 4.1 | 90.1 ± 4.9 | 3.7 ± 0.6 | 5.1 ± 0.9 |
| 2 | 96.8 ± 6.9 | 59.7 ± 11.8* | 5.6 ± 1.9 | 16.1 ± 3.7 |
| 4 | 79.3 ± 6.4* | 8.7 ± 1.6* | 20.1 ± 6.5* | 220.5 ± 60.7* |

Values represent means ± SEM of n = 5.
*Giardia lamblia* trophozoites were incubated with gangliosides containing nutrients at the concentration of 0 (control), 0.001, 0.01, 1, 2, and 4 $\mu$g/ml (N-acetyl neuraminic acid) for 24 hrs and 48 hrs.
[a]Expressed as a % of control containing zero ganglioside.
[b]Expressed as a % of live trophozoites at each concentration.
*Indicates the significant difference in comparison to control. Significant effects of gangliosides were identified by one-way analysis of variance procedures.

The growth of trophozoites in vitro was significantly reduced in the presence of gangliosides. After a 24 hr incubation, there was a 20% reduction of live trophozoites in cultures containing 4 µg/ml of ganglioside, compared to control cultures. After 48 hr incubation, in cultures containing 2 and 4 µg/ml ganglioside, the number of live trophozoites decreased by 40% and 91%, respectively, compared to control cultures (Table 3). A concomitant increase in the number of dead trophozoites, expressed as a percent of live trophozoites, was observed in cultures containing 4 µg/ml ganglioside after 24 and 48 hr incubation.

Gangliosides were extracted from the whole ganglioside enriched preparation to determine whether the effects observed could be attributed to only the ganglioside constituents of the preparation. Ganglioside fraction was provided at the level of 0 (control), 4, 8, 10, 12, 14, 16 and 20 µg/ml to each flask containing $5 \times 10^5$ trophozoites and incubated for 24 hrs and 48 hrs. After 24 hr incubation, significant reduction of trophozoite growth was observed in cultures containing more than 12 µg/ml of ganglioside. After 48 hr incubation, in cultures containing 8, 10, 12, 14 and 16 µg/ml ganglioside, the number of live trophozoites decreased by 36%, 45%, 77%, 98%, and 99%, respectively, compared to control cultures, as shown in Table 4 and FIG. 4.

Figure 4:
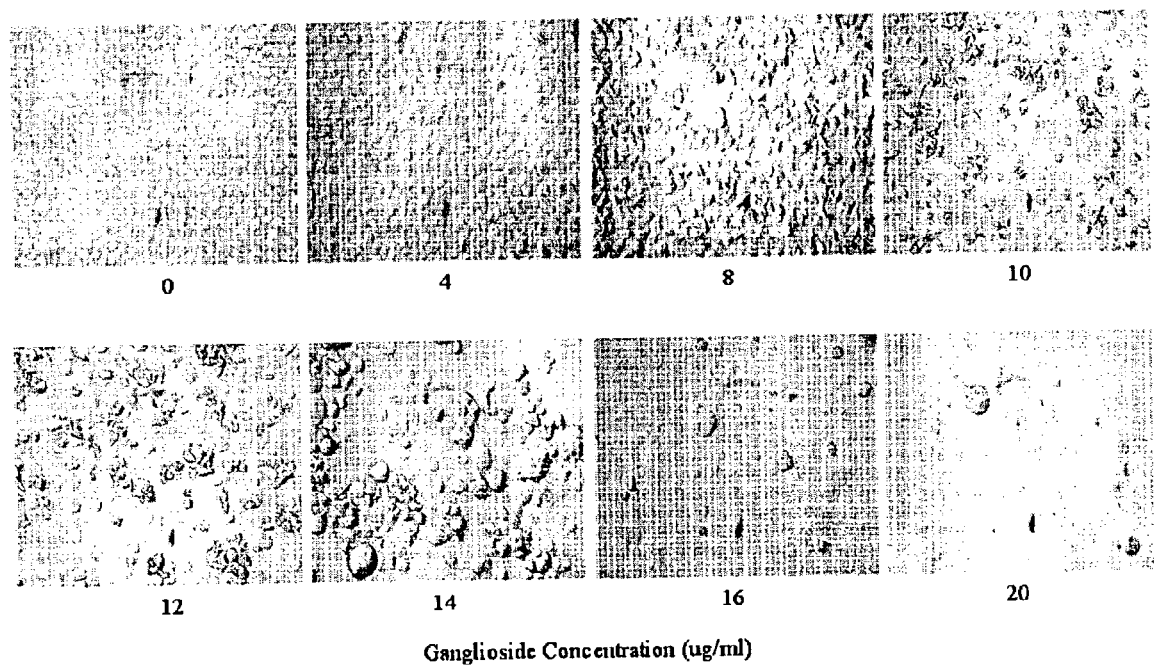
FIG. 4 photographically illustrates the effect of gangliosides on the growth of *Giardia lamblia* trophozoites during a 48 hour incubation in vitro.

FIG. 4 illustrates the effect of gangliosides on the growth of *Giardia lamblia* trophozoites during 48 hr incubation in vitro. *Giardia lamblia* trophozoites were incubated for 48 hours with gangliosides extracted from the crude ganglioside preparation at a concentration of 0 (control), 4, 8, 10, 12, 14, 16, and 20 µg/ml (N-acetyl neuraminic acid). (Magnification×200).

As seen in FIG. 4, no live trophozoites were found at a ganglioside concentration of 20 µg/ml. These results indicate that the growth of trophozoites was dependant on the dose of ganglioside.

TABLE 4

Effect of gangliosides on the growth of *Giardia lamblia* trophozoites during 48 hr incubation in vitro

| Significance | Live Trophozoites[a] ($p < 0.0003$) | Dead trophozoites[b] ($p < 0.002$) |
|---|---|---|
| Ganglioside Conc. (µg/ml) | | |
| 0 | 100 | 0.8 ± 0.5[b] |
| 4 | 90.5 ± 3.4[a] | 1.2 ± 0.6[b] |
| 8 | 63.8 ± 3.2[b] | 1.2 ± 0.7[b] |
| 10 | 55.0 ± 5.7[b] | 3.9 ± 1.7[b] |
| 12 | 22.6 ± 8.0[c] | 45.6 ± 9.6[b] |
| 14 | 1.3 ± 0.8[d] | 884.1 ± 351.8[b] |
| 16 | 0.2 ± 0.1[d] | 6232.6 ± 1362.4[a] |
| 20 | 0.0 ± 0.0[d] | — |

Values represent means ± SEM of n = 3.
*Giardia lamblia* trophozoites were incubated with gangliosides extracted from the crude ganglioside preparation at a concentration of 0 (control), 4, 8, 10, 12, 14, 16, and 20 µg/ml (N-acetyl neuraminic acid) for 48 hrs.
[a]expressed as a % of control containing zero ganglioside.
[b]expressed as a % of live trophozoites at each concentration.
No live trophozoites were found at the concentration of 20 µg/ml, where no values (–) were given (see FIG. 4).
Values without a common letter in each column are significantly different between ganglioside concentrations. Significant effects of gangliosides were identified by one-way analysis of variance procedures.

Discussion. This is the first study to examine the effects of dietary gangliosides on the course of gastrointestinal protozoan infections. Mice fed either a high (1%, w/w) or a low (0.1%, w/w) concentration of ganglioside containing diets released significantly less cysts in the feces (a 3 $\log_{10}$ reduction) and had significantly reduced trophozoite burden in the small intestine (a 1.7 $\log_{10}$ reduction). Delay in the onset of cyst release and shorter duration of cyst release was also observed in mice fed dietary gangliosides. Our results indicate that ganglioside content in the diet of ~0.1% (w/w, 0.02% as NANA) was sufficient to significantly alter the course of giardiasis in mice. The mechanisms for this anti-parasite effect of ganglioside remain to be elucidated.

This invention illustrates that it is possible for gangliosides to: (i) inhibit the adherence of the trophozoites to the intestinal epithelium by changing the membrane lipid environment of the mucosa; (ii) affect the metabolic machinery of the parasites, influencing multiplication and/or encystment; (iii) have direct toxic effects on the trophozoites; and (iv) modulate host immune function in the small intestine.

The brush border membrane contains approximately 20% glycosphingolipid (Forstner and Wherrett, 1973) and a dominant intestinal ganglioside is GM3 (Iwamori et al., 1984). The pattern and concentration of ganglioside is species and tissue-specific and is also influenced by age of the host (Iwamori et al., 1984). Dietary manipulation also affects the ganglioside profiles of the intestinal mucosa.

In the present Example, mice were fed a ganglioside diet for two weeks prior to exposure to *G. muris*, providing ample time for change in ganglioside content of the mouse small intestine to occur. It is possible that introduction of a more acidic sugar, GD3, and proportional reduction of GM3 in the mucosa may alter ability of trophozoites to attach to the mucosal surface, thereby affecting normal reproduction behaviour of the parasites. Gangliosides acting as parasite receptors have been reported for *Theileria sergenti* (Watarai et al., 1995). Preliminary results suggest that not only dietary mixtures of gangliosides but also isolated GD3, affect parasite survival in vivo and in vitro.

Dietary gangliosides may also change anti-parasite host immune response. Further, incorporation of dietary gangliosides into the enterocyte plasma membrane may interfere with the transport and expression of sIgA, which has been shown to be important in protection against *G. muris* infection (Underdown et al., 1981).

This Example establishes that gangliosides directly affects parasite growth. Cultivation of *G. lamblia* trophozoites for 24 hr and 48 hr, in the presence of different concentrations of ganglioside significantly reduced the number of live trophozoites in the cultures. Unlike wheat germ agglutinin arresting the trophozoite cell cycle (Ortega-Barria et al., 1994), the effect of ganglioside was irreversible because the majority of trophozoites in cultures were lysed. The present results indicate that ganglioside may be directly toxic to *G. lamblia* trophozoites. Lysis of *G. lamblia* trophozoites by lipolytic product of non-immune component of human milk has been reported (Gillin et al., 1985; Reiner et al., 1986). However, these studies did not examine the potential anti-parasite effect of gangliosides present in human milk. The results of the instant example suggest that gangliosides present in milk may also participate in lysis of *G. lamblia* trophozoites.

*G. lamblia* trophozoites are unable to synthesize their own phospholipids and sterols de novo (Jarrol et al., 1981), but are able to take up exogenous lipids into the membrane by trans- and inter-esterification (Gibson et al., 1999; Stevens et al., 1997.). Thus, host lipids play a critical role for metabolism and long-term survival of the parasite. Gangliosides, GM2 and GD1a, have been identified as membrane components of another gastrointestinal parasite, *Entamoeba histolytica* (Sorice et al., 1996). It is, therefore, likely that the exogenous gangliosides are taken up by trophozoites which could exchange the ganglioside composition in the trophozoite cell membrane and disturb the structural components of the trophozoites, leading to lysis of the parasite.

In conclusion, the results of this Example demonstrate that dietary gangliosides administered before and during giardiasis, significantly alter the course of *G. muris* infection in mice and influence the growth of *G. lamblia* trophozoites in vitro. These dietary gangliosides cause lysis of the parasite. These data suggest that increasing ganglioside content in the diet may have beneficial effects in the control of giardiasis and amoeba infections.

EXAMPLE 2

Milk Fraction A containing Gangliosides is Prophylactic against Giardia Infection in vivo, and in vitro.

Figure 5:
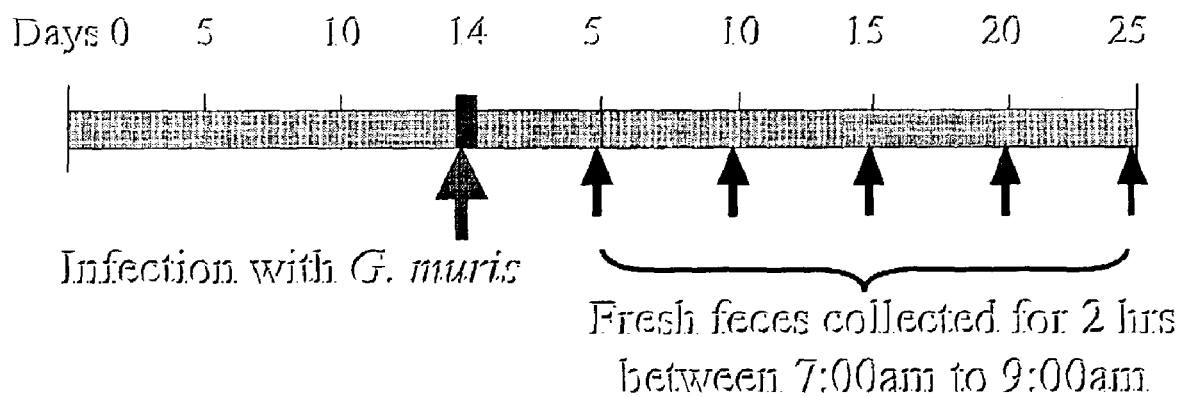
FIG. 5 depicts the experimental protocol used in Example 2.

In vivo. 5 weeks old pathogen free CD-1 mice were fed experimental diets with (High or Low concentration) and without Fraction A for 14 days. Mice were then infected with 10,000 *Giardia muris* by gastric incubation and continued on the same diets for 25 days post infection, as shown in FIG. 5. Fresh feces were collected for 2 h for every 5 day period for 25 days to measure the cyst produced in feces. Mucosa from small intestine of jejunum and ileum was scraped to count the number of trophozoites in the small intestine of infected mice at 10 days post infection.

In vitro. This study was performed to determine if Fraction A is directly toxic to the parasite. Several dilutions of Fraction A was added to the media at the concentration of 0, 0.001, 0.01, 0, 1, 1, 2, and 4 ug/ml and incubated for 24 hours and 48 hours after inoculation with 500,000 *Giardia lamblia* trophozoites.

Table 5 provides the composition of Fraction A, illustrating the amount of total lipid, calcium and lactose present in 100 g of Fraction A on a dry weight basis. The ganglioside and phospholipid content of the lipid fraction is broken down into specific components. In Table 5, all abbreviations used are those defined previously, and additionally: % GG means percent of total gangliosides; % PL means percent of total phospholipids; x-1, x-2 and x-3 are gangliosides; LPC: lysophosphatidylcholine; SM: sphingomyelin; PC: phosphatidylcholine; LPE; lysophosphatidylethanolamine; PS: phosphatidylserine; PI: phosphatidylinositol; PE: phosphatidyl ethanoloamine.

TABLE 5

Composition of Fraction A

| Fraction A | 100 g | | |
|---|---|---|---|
| Total Lipids(g) | 23.00 | | |
| | | (g) | |
| Gangliosides (as NANA amt) | | 0.82 | (% GG) |
| | GM3 | | 4.50 |
| | x-1 | | 4.60 |
| | x-2 | | 0.80 |
| | GD3 | | 79.90 |
| | GD1b | | 9.00 |
| | x-3 | | 1.20 |
| | | (g) | |
| PL (as 'P') | | 0.49 | (% PL) |
| | LPC | 0.036 | 7.3 |
| | SM | 0.013 | 2.7 |
| | PC | 0.012 | 2.5 |
| | LPE | 0.093 | 19.0 |
| | PS | 0.149 | 30.4 |
| | PI | 0.136 | 27.8 |
| | PE | 0.050 | 10.2 |
| | | 0.49 | 99.9 |
| Neutral lipid | | 0.04 | |
| Cholesterol | | 0.08 | |
| Ca(g) | | 10.00 | |
| Lactose(g) | | 65–70 | |

Figure 6:
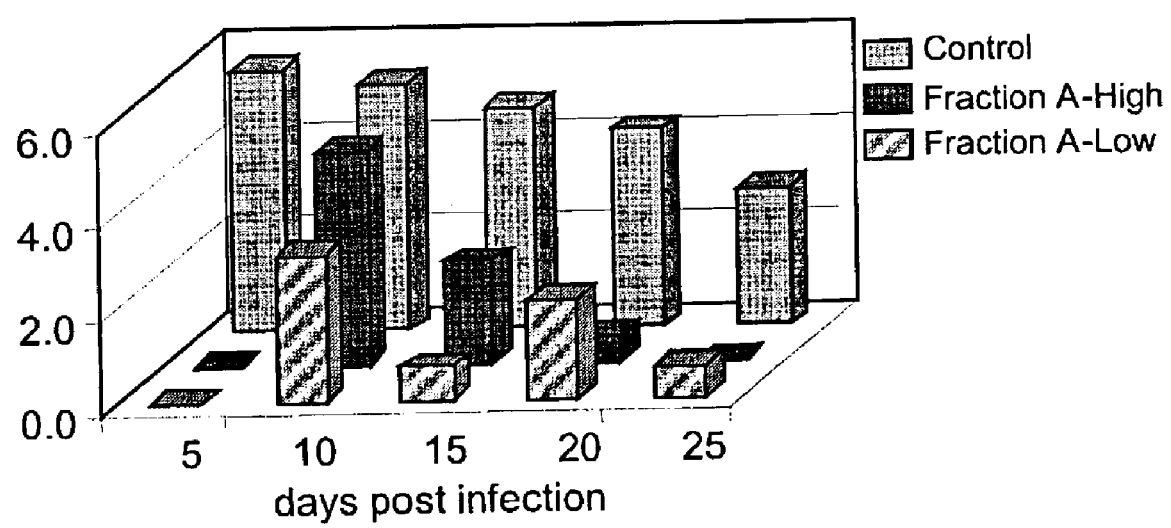
FIG. 6 shows the effect of Fraction A on the course of *Giardia muris* infection in mice in Example 2. The vertical axis shows the number of cysts per gram of feces in log-units.

Mice fed Fraction A-High or Fraction A-Low diets were without parasite cysts on day 5 after infection, as shown in FIG. 6. This figure shows the effect of Fraction A on the course of *Giardia muris* infection in mice. Specifically, the number of cysts per gram of feces (in log-units) found in infected mice at 1, 50, 15, 20 and 25 days post-infection is illustrated. The values (means, n=10, except day 25, n=5) were derived from two independent experiments. Mice fed Fraction A-High or Fraction A-Low were absent of parasites on day 5 after infection. Mice fed either of the Fraction A diets had reduced numbers of cysts in the feces during 25 days post-infection, with rapid elimination of the parasites, compared to mice fed a control diet. These two Fraction A containing diets drastically reduced in the number of cysts in the feces during 25 days post infection with rapid elimination of the parasites compared to mice fed a control chow diet.

Figure 7:
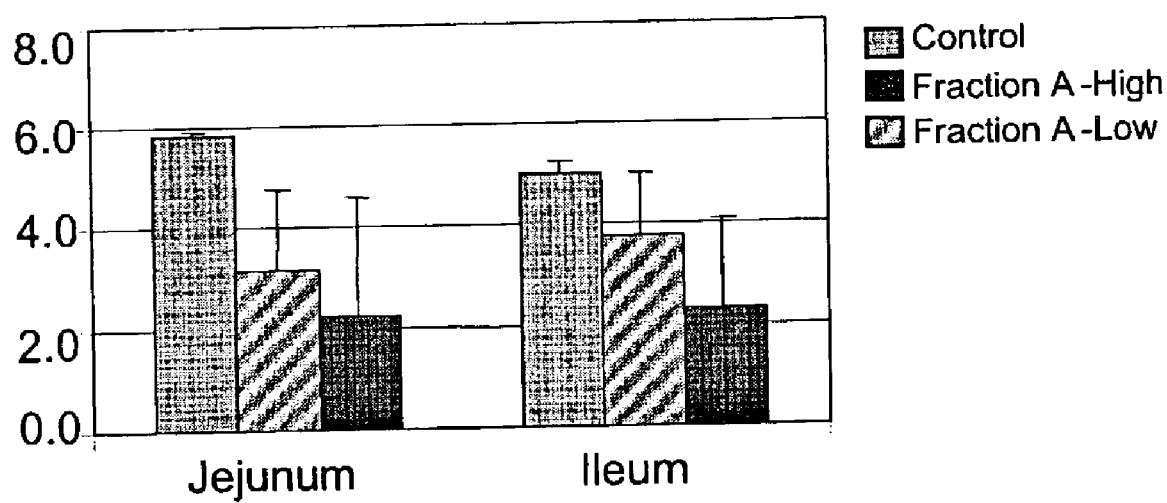
FIG. 7 illustrates the effect of Fraction A on *Giardia muris* replication in the small intestine of mice at 10 days post-infection.

Mice fed either High or Low levels of Fraction A significantly reduced in the number of trophozoites in the small intestine at 10 days post infection compared to mice fed the control diet, as shown in FIG. 7. This figure shows the effect of Fraction A on *Giardia muris* replication in the small intestine of mice at 10 days post-infection. The vertical axis indicates the number of trophozoites per cm of intestine (in log-units). The values are mean±SD. Mice fed either of the Fraction A diets showed a reduction in the number of trophozoites in the small intestine at 10 days post infection, compared with mice fed a control diet.

Figure 8:
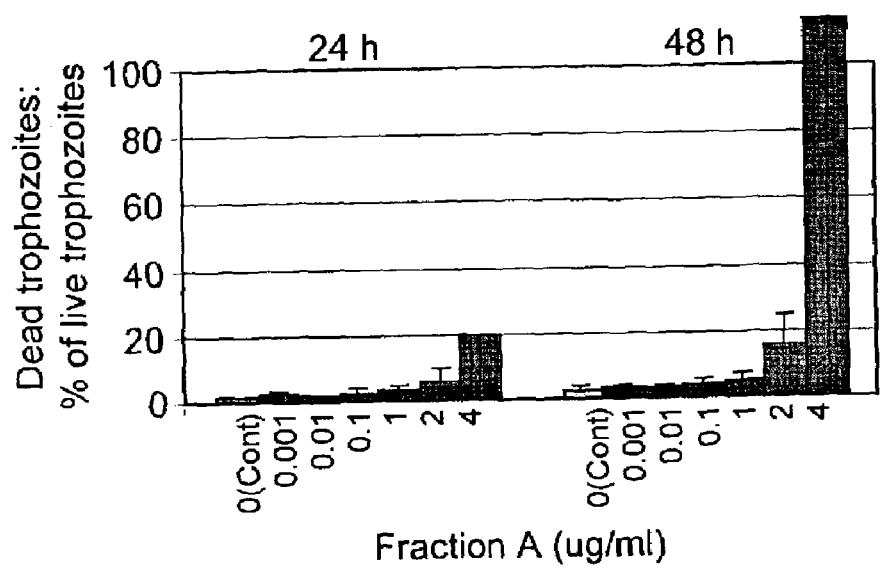
FIG. 8 illustrates the effect of Fraction A on replication of *Giardia lamblia* trophozoites during 24 and 48 hour incubations in vitro.

The number of dead trophozoites significantly increased at the concentration of 4 ug/ml after 24 h and 2 ug/ml and 4 ug/ml after 48 h of in vitro culture, as shown in FIG. 8. The overall cyst output during the first 20 days of infection in control (chow group) was approximately $10^8$/mouse, while that of Fraction A-Low and Fraction A-High groups was approximately $10^4$/mouse, an incredible four-log difference between the groups. These results indicate that Fraction A results in significant control of parasite replication in animals fed diets containing Fraction A at a low level. Very small amounts of Fraction A are toxic to Giardia and thus, Fraction A shows a greater efficacy than drugs currently used to treat Giardia infections.

Figure 9:
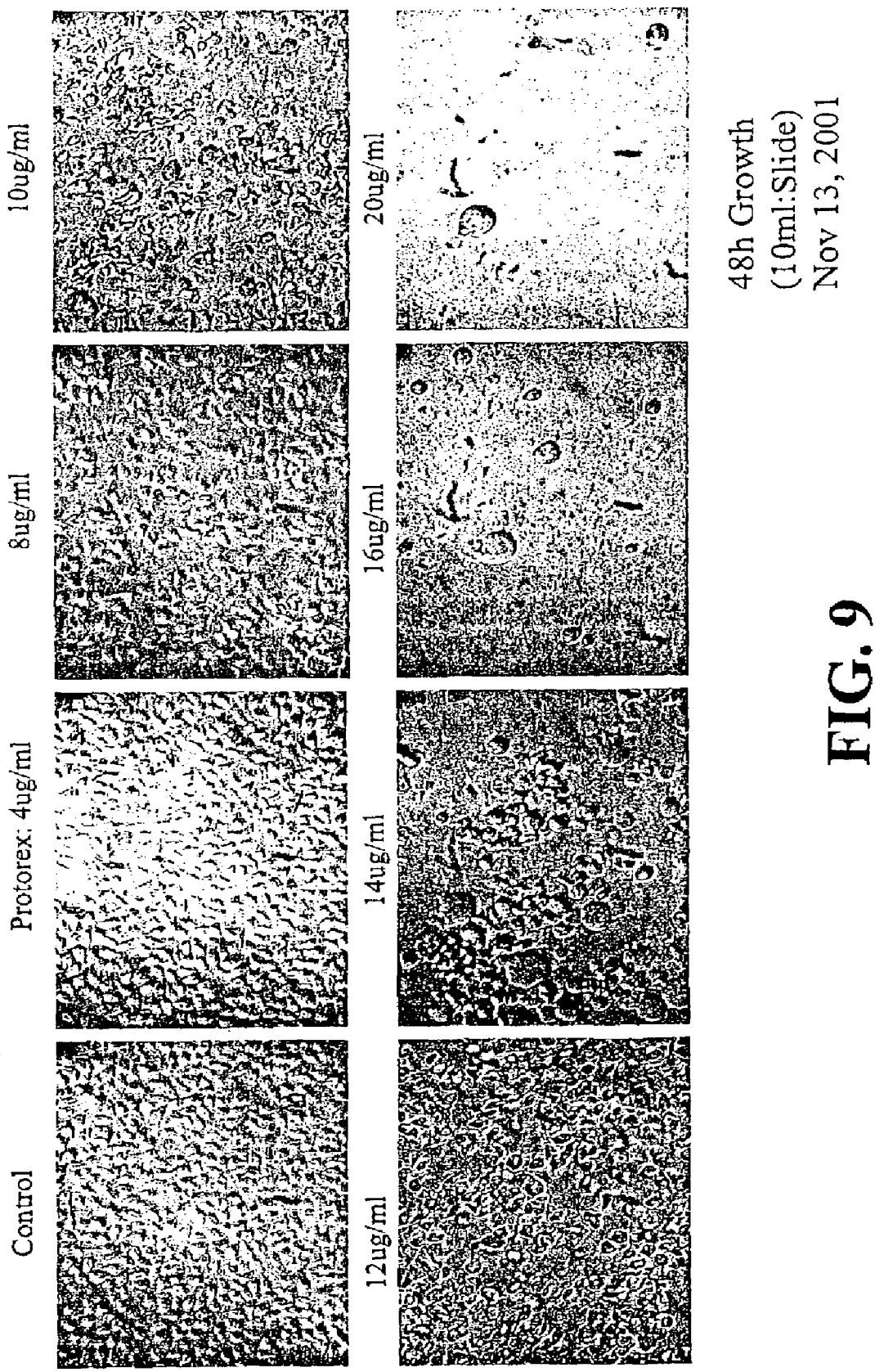
FIG. 9 illustrates the levels of the inventive lipid formulation supplementation of Protorex required to reduce Giardia growth.

FIG. 9 illustrates the levels of the inventive lipid formulation supplementation of Protorex required to reduce Giardia growth.

Figure 10:
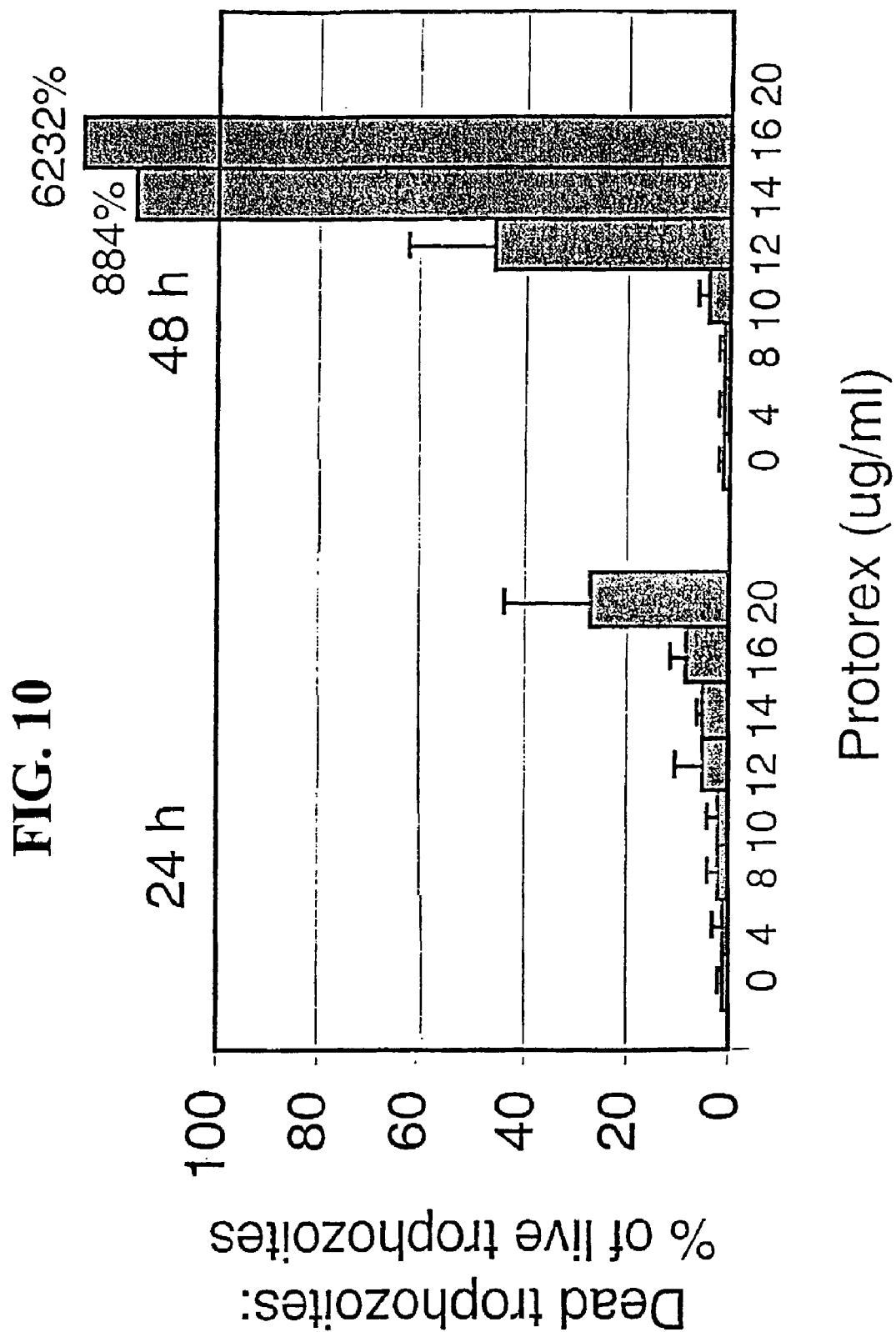
FIG. 10 shows the effect of the inventive lipid formulation supplementation on replication of *Giardia lamblia* trophozoites during 24 and 48 hour incubations in vitro, showing the number of dead trophozoites as a percentage of live trophozoites.

FIG. 10 shows the effect of the inventive lipid formulation supplementation of replication of *Giardia lamblia* trophozoites during 24 and 48 hour incubations in vitro, showing the number of dead trophozoites as a percentage of live trophozoites.

Figure 11:
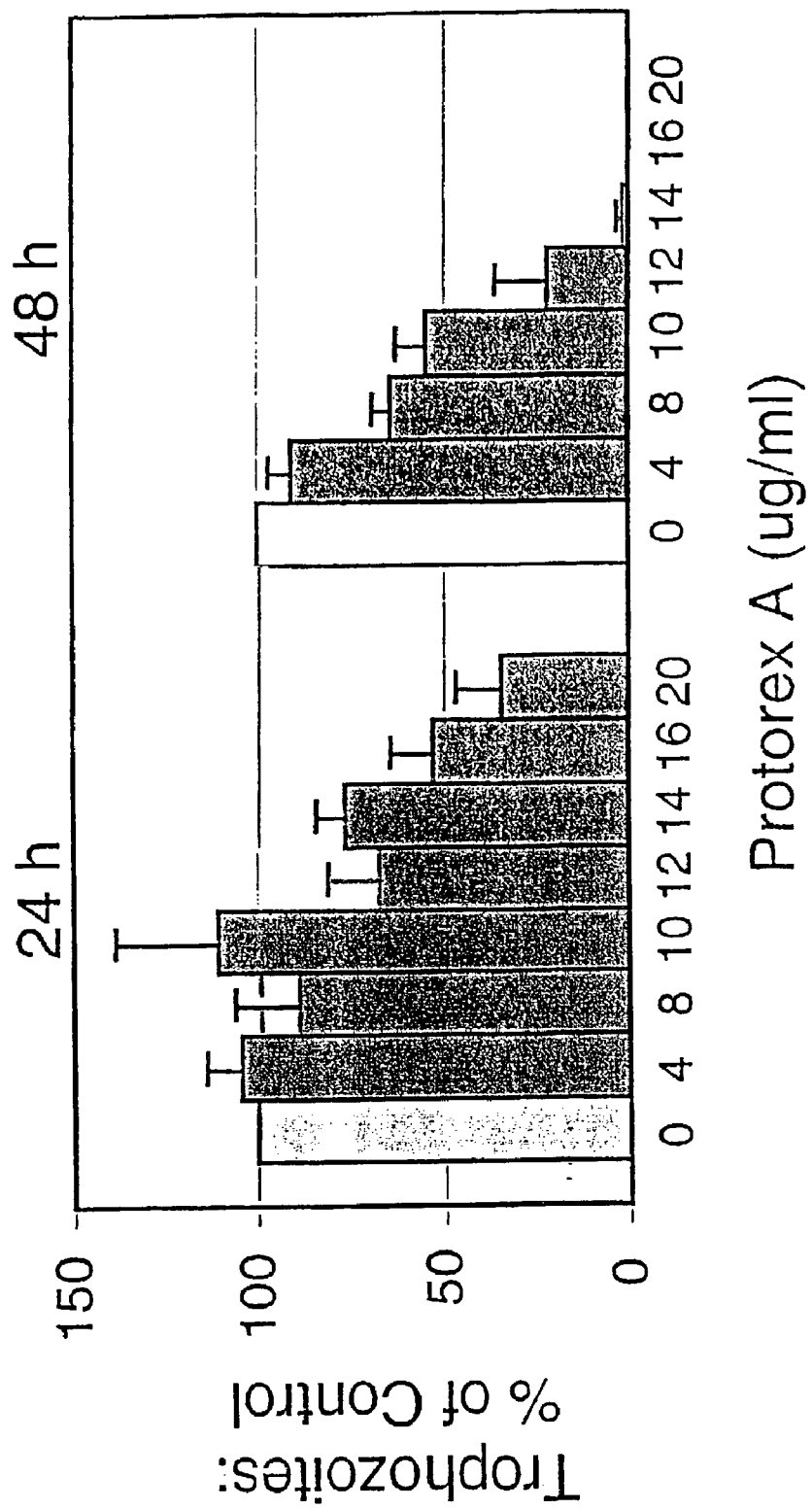
FIG. 11 illustrates the effect of supplementation with the inventive lipid formulation on replication of *Giardia lamblia* trophozoites during 24 and 48 hour incubations in vitro, showing trophozoites as a percentage of control.

FIG. 11 illustrates the effect of supplementation with the inventive lipid formulation on replication of *Giardia lamblia* trophozoites during 24 and 48 hour incubations in vitro, showing trophozoites as a percentage of control.

Figure 12:
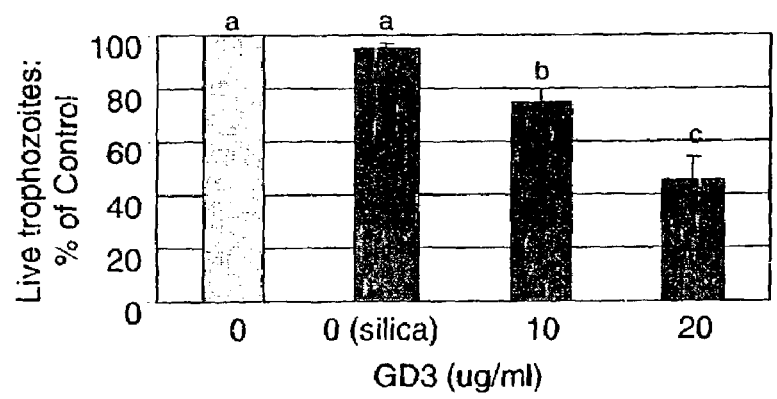
FIG. 12 illustrates the effect of GD3 (a specific ganglioside) on *Giardia lamblia* trophozoites during a 48 hour incubation in vitro.

FIG. 12 illustrates the effect of GD3 (a specific ganglioside) on *Giardia lamblia* trophozoites during a 48 hour incubation in vitro. This data illustrates live trophozoites decrease as a percent of control in a dose-dependent manner with concentrations of GD3.

Figure 13:
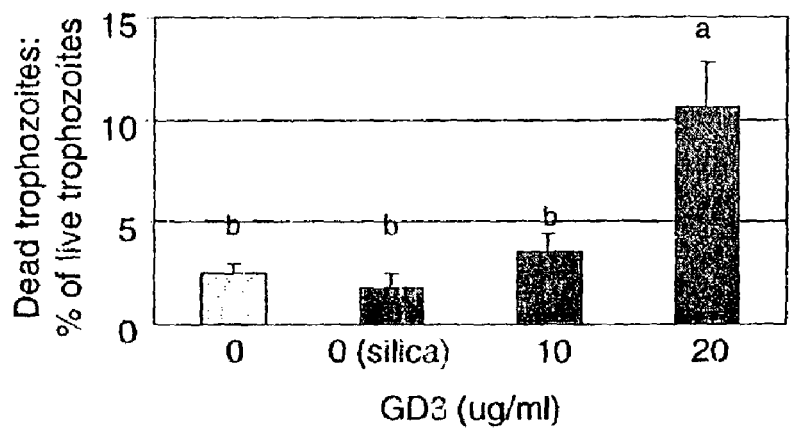
FIG. 13 illustrates the effect of GD3 on *Giardia lamblia* trophozoites during a 48 hour incubation in vitro.

FIG. 13 illustrates the effect of GD3 on *Giardia lamblia* trophozoites during a 48 hour incubation in vitro. The data shown illustrate that dead trophozoites increase as a percentage of live trophozoites, in a manner proportional to the concentration of GD3 in the incubation media.

EXAMPLE 3

Separation of Gangliosides from Fraction A

Fraction A, having the composition described above in Table 5, was obtained and gangliosides were separated were separated therefrom using the following method. The separated ganglioside fraction so obtained may be used in a supplementation regime according to the invention. Alternatively, individual gangliosides obtained from the separated fraction may be used in a supplementation regime according to the invention.

Total lipids were extracted from the ganglioside enriched preparation of Fraction A using the Folch method (Folch and Sloane-Stanley, 1957). The ganglioside-containing upper phase was transferred and the lower phase was washed once with Folch upper phase solution (chloroform/methanol/water, Mar. 48, 1947 by vol.). The combined ganglioside-containing fractions were passed through Sep-Pak™ C18 reverse-phase cartridges (Waters Corporation, Milford, Mass., USA), eluted with methanol and chloroform and methanol 2:1 (v/v), and dried completely under vacuum at 23° C. using a rotary evaporator. Ganglioside (NANA) content was measured as described by Suzuki (1964).

EXAMPLE 4

Effect of Ganglioside GD3 on Growth of *G. lamblia* Trophozoites During 48 hr Incubation In Vitro.

In this example, preparation of culture medium containing ganglioside GD3 was conducted as follows. Individual ganglioside from the ganglioside extract was separated by thin layer chromatography on silica-gel G-plates (20×20 cm) using a developing system, chloroform/methanol/28% (w/v) $NH_4OH/H_2O$ (60:35:7:3, by vol). The corresponding GD3 band was eluted with chloroform/methanol (2:1, v/v) and dried under nitrogen. GD3 was further purified using silica-gel high performance thin layer chromatography (HPTLC; Whatman Inc., Clifton, N.J., USA) in a solvent system of chloroform/methanol/0.2% (w/v) $CaCl_2.2H_2O$ (55/45/10, by vol). GD3 was eluted with the Folch upper phase by chloroform/methanol/$H_2O$ (3:48:47) and dried under nitrogen. GD3 was then diluted with $H_2O$ and filtered through 0.22 µm filters (Millex-GP filters, Millipore Corp) fitted to a 3 ml syringe. Silica-gel containing no ganglioside was extracted from the beginning using the same procedure. This is the control for potential carry-over of solvent used in the extraction.

*G. lamblia* (WB strain) trophozoites were cultured in Diamond's TYI-S-33. *G. lamblia* trophozoites ($5\times10^5$) were inoculated in 12.5 $cm^2$ tissue culture flasks in the total volume of 40 ml. GD3 was provided at the concentration of 0 (control), 10 and 20 µg/ml in 12.5 $cm^2$ tissue culture flasks. The cultures were incubated for 48 hr at 37° C. in 5% $CO_2$, and the number of live and dead (no flagellar movement) trophozoites determined using a hemocytometer.

Effect of Ganglioside GD3 on the Growth of *G. Lamblia* Trophozoites.

Figure 14:
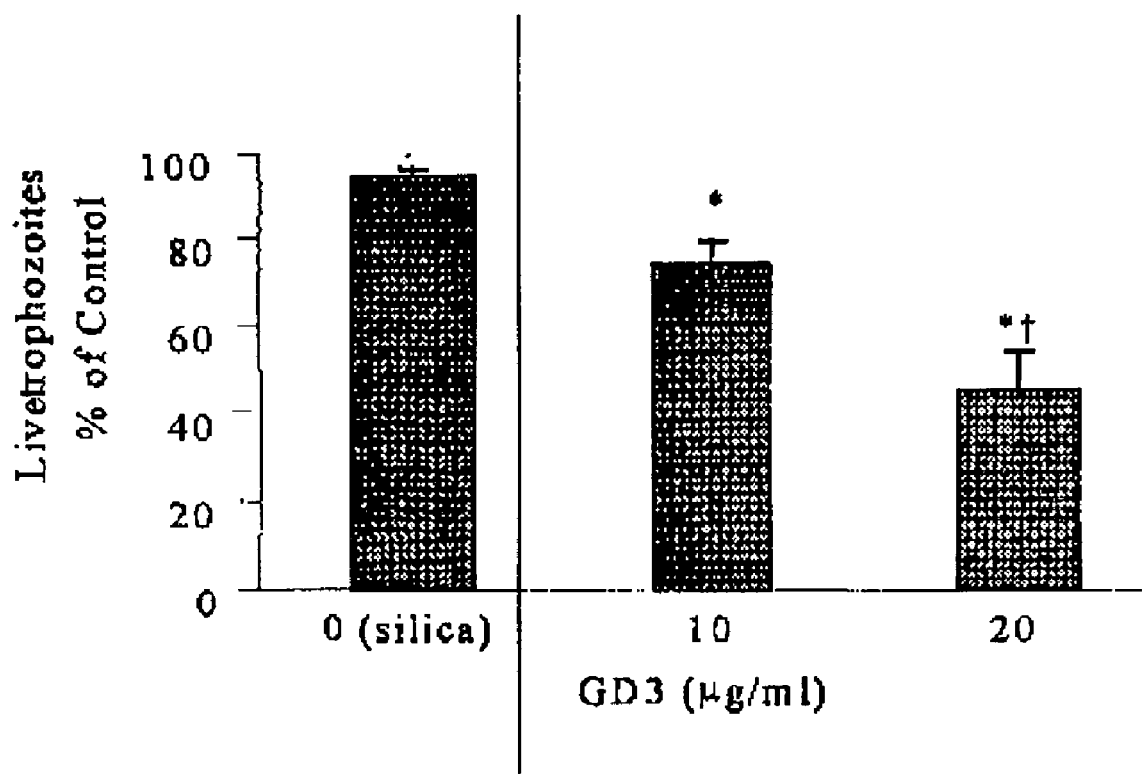
FIG. 14 shows the effect of ganglioside GD3 on the growth of *G. lamblia* trophozoites during 48 hr incubation in vitro.

FIG. 14 illustrates that, after 48 hr incubation with GD3, a significant reduction of live trophozoites was observed in cultures containing 10 and 20 µg/ml ganglioside, 25% and 55%, respectively, compared to control cultures. Values represent means±SEM of n=3. *Giardia lamblia* trophozoites were incubated with GD3 at a concentration of 0 (control), 10 and 20 µg/ml (N-acetyl neuramine acid) for 48 hrs. Live trophozoites are expressed as a % of control containing zero ganglioside. Data with 0 (silica) is the control for possible carry-over of solvent used in the extraction. Silica gel containing no ganglioside was extracted by the same procedure used for GD3 extraction in the methods. Significant effect of GD3 was identified by one-way analysis of variance procedures, $p<0.003$. Values with * were significantly different from control. Values with †were significantly different when Giardia was cultured with 10 µg/ml GD3.

The above-described embodiments of the present invention are intended to be examples only. Alterations, modifications and variations may be effected to the particular embodiments by those of skill in the art without departing from the scope of the invention, which is defined solely by the claims appended hereto.

What is claimed is:

1. A method for treatment or prevention of a parasitic infection in a subiect in need thereof comprising the step of providing a ganciliioside to said subject for oral consumption, wherein said parasitic infection comprises a *Giardia* infection.

2. The method according to 1, wherein said ganglioside is selected from the group consisting of: GD3, GM1, GM2, GM3, GD1b, and combinations thereof.

3. The method according to 1, wherein said ganglioside is provided in the form of a supplemented liquid or food.

4. The method according to 3, wherein said supplemented liquid or food is selected from the group consisting of infant formula, baby food, baby cereal, juice, dehydrated food, and bottled water.

5. The method of claim 2, wherein the ganglioside comprises about 80% GD3, 9% GD1b, and 5% GM3 on a weight/weight basis.

6. A method for treatment or prevention of a parasitic infection in a subject in need thereof comprising the step of providing a ganglioside to said subject for oral consumption, wherein said parasitic infection comprises a protozoan infection selected from the group consisting of *Giardia intestinails, Entamoeba histolytica, Cryptosporidium parvum, Eimeria tenella, Balantidium coli, intestinal lobosea, intestinal sporozoea,* and *intestinal zoomastigophorea* infection.

7. The method according to claim 6, wherein said ganglioside is selected from the group consisting of: GD3, GM1, GM2, GM3, GD1b, and combinations thereof.

8. The method according to claim 6, wherein said ganglioside is provided in the form of a supplemented liquid or food.

9. The method according to 8, wherein said supplemented liquid or food is selected from the group consisting of infant formula, baby food, baby cereal, juice, dehydrated food, and bottled water.

10. The method of claim 7 wherein the ganglioside comprises about 80% GD3, 9% GD1b, and 5% GM3 on a weight/weight basis.

* * * * *

UNITED STATES PATENT AND TRADEMARK OFFICE
CERTIFICATE OF CORRECTION

PATENT NO. : 6,998,392 B2  
APPLICATION NO. : 10/404095  
DATED : February 14, 2006  
INVENTOR(S) : Clandinin et al.

Page 1 of 1

It is certified that error appears in the above-identified patent and that said Letters Patent is hereby corrected as shown below:

Column 18,  
Line 27, delete "subiect" and insert -- subject --;  
Line 28, delete "gancilioside" and insert -- ganglioside --;  
Lines 31 and 34, insert -- claim -- between "to" and "1";  
Line 36, insert -- claim -- between "to" and "3";  
Lines 47 and 48, delete "intestinails" and insert -- intestinalls --; and  
Line 57, insert -- claim -- between "to" and "8".

Signed and Sealed this

Twentieth Day of June, 2006

JON W. DUDAS  
*Director of the United States Patent and Trademark Office*

UNITED STATES PATENT AND TRADEMARK OFFICE
CERTIFICATE OF CORRECTION

PATENT NO. : 6,998,392 B2 Page 1 of 1
APPLICATION NO. : 10/404095
DATED : February 14, 2006
INVENTOR(S) : Michael Thomas Clandinin et al.

It is certified that error appears in the above-identified patent and that said Letters Patent is hereby corrected as shown below:

Column 18, lines 47 & 48, delete "intestinails" (or "intestinalls", as incorrectly noted on the June 20, 2006 certificate of correction) and insert therefor --intestinalis--.

Signed and Sealed this

Twelfth Day of December, 2006

JON W. DUDAS
*Director of the United States Patent and Trademark Office*